United States Patent [19]

Haussmann

[11] Patent Number: 5,505,855
[45] Date of Patent: Apr. 9, 1996

[54] PROCESS FOR PURIFICATION OF NON-AQUEOUS VISCOUS ORGANIC COMPOUNDS

[75] Inventor: Christian U. Haussmann, Seattle, Wash.

[73] Assignee: Gas Research Institute, Chicago, Ill.

[21] Appl. No.: 382,671

[22] Filed: Feb. 2, 1995

[51] Int. Cl.⁶ .................................................. B01D 61/00
[52] U.S. Cl. ........................... 210/652; 210/651; 210/774; 585/818; 208/290
[58] Field of Search .................................... 210/651, 652, 210/653, 654, 774, 167; 585/818, 819; 208/290

[56] References Cited

U.S. PATENT DOCUMENTS

| | | | |
|---|---|---|---|
| 3,556,990 | 1/1971 | Gulko | 210/651 |
| 3,651,617 | 3/1972 | Hodgson . | |
| 4,000,065 | 12/1976 | Ladha et al. | 210/652 |
| 4,240,914 | 12/1980 | Iwama | 210/257.2 |
| 4,357,236 | 11/1982 | Krueger | 210/167 |
| 4,802,988 | 2/1989 | Bartels et al. | 210/651 |
| 4,814,088 | 3/1989 | Kutowy et al. | 210/651 |
| 4,902,417 | 2/1990 | Lien | 210/321.74 |
| 4,946,939 | 8/1990 | Murphy | 210/651 |
| 5,030,750 | 7/1991 | Kuzira et al. | 562/554 |
| 5,034,134 | 7/1991 | George et al. | 210/651 |
| 5,167,826 | 12/1992 | Eaton | 210/651 |
| 5,194,159 | 3/1993 | George et al. | 210/654 |
| 5,256,297 | 10/1993 | Feimer et al. | 210/651 |
| 5,269,933 | 12/1993 | Jehle et al. | 210/652 |
| 5,276,244 | 1/1994 | Lin et al. | 210/651 |
| 5,281,337 | 1/1994 | Chou et al. | 210/654 |

*Primary Examiner*—Ana M. Fortuna
*Attorney, Agent, or Firm*—Speckman, Pauley & Fejer

[57] ABSTRACT

A process for purification of a substantially non-aqueous, viscous, contaminated organic liquid, in particular tri-ethylene glycol, comprising heating the contaminated organic liquid to a temperature in the range of about 70° C. to about 100° C. and passing the contaminated organic liquid through a reverse osmosis membrane at a pressure in the range of about 400 psig to 650 psig. As a result of passing through the reverse osmosis membrane, a purified organic liquid is formed on one side of the membrane and a retentate with contaminants removed from the contaminated organic liquid is formed on the other side of the reverse osmosis membrane.

11 Claims, 2 Drawing Sheets

PROCESS FOR PURIFICATION OF NON-AQUEOUS VISCOUS ORGANIC COMPOUNDS

BACKGROUND OF THE INVENTION

1. Field of the Invention

This invention relates to a process for purification of substantially non-aqueous, viscous, contaminated organic liquids with reverse osmosis membranes at conditions other than "reverse osmosis conditions". More particularly, this invention relates to a process for purification of non-aqueous, contaminated higher glycols, in particular tri-ethylene glycol.

2. Description of Prior Art

This invention addresses the treatment of higher glycols, such as ethylene glycol, di-ethylene glycol, and, in particular, tri-ethylene glycol which is utilized in gas processing operations. Known methods for purifying contaminated tri-ethylene glycol include distillation, filtration and absorption with activated charcoal; however, capital and operating costs for such known processes are relatively high. In addition, filtration is only effective for suspended solids removal which is not a major pollutant of tri-ethylene glycol while activated charcoal absorption only removes hydrocarbons and, thus, is not effective in removing inorganics such as chlorides and sulfides. Removal of chlorides from tri-ethylene glycol is of critical importance.

It is also known to employ reverse osmosis membranes in purifying antifreeze, which is dilute ethylene or di-ethylene glycol. However, antifreeze which is recycled for purification is in a dilute state, typically containing 40–70% water, rendering it much easier to process than non-aqueous, contaminated glycols. Undiluted glycols are much more viscous, requiring specialized equipment assembly and processing techniques.

U.S. Pat. No. 4,902,417 to Lien teaches a spiral-wound membrane cartridge for use in ultrafiltration and reverse-osmosis separation equipment which includes a feed layer, a membrane layer and a permeate carrier layer. Such cartridges are indicated to be particularly useful with feed mixtures including suspended solids, as well as with aqueous mixtures of partially soluble solids, such as glycols, oils and proteins.

U.S. Pat. No. 3,651,617 to Hodgson teaches a regeneration system employing reverse osmosis for recovery of desiccants such as ethylene glycol, di-ethylene glycol and tri-ethylene glycol used for dehydrating natural gas from hygroscopic liquids. In accordance with the teachings of the '617 patent, a water-rich desiccant is pressurized in excess of its osmotic pressure and passed through a semi-permeable membrane of selective permeability, thereby removing water from the water-rich desiccant.

U.S. Pat. No. 4,000,065 to Ladha et al. teaches a process and apparatus for separating aqueous streams contaminated with minor amounts of organic materials using reverse osmosis. The use of reverse osmosis in conjunction with separation of lower glycols from relatively dilute solutions is also taught by U.S. Pat. No. 5,281,337 to Chou et al. which teaches a membrane and membrane support layer for separating charge systems such as aqueous mixtures of ethylene glycol in a reverse osmosis module; U.S. Pat. No. 5,167,826 to Eaton which teaches a process for recycling used engine coolant, that is glycol-based coolants, using reverse osmosis, the disclosed membrane allowing ethylene glycol and water to pass through at pressures at between 50 and 500 psi and temperatures preferably below 100° F.; and U.S. Pat. No. 5,194,159 to George et al. which teaches a process for reclaiming lower glycols from operative fluids, such as antifreeze, using reverse osmosis, where the operative fluid preferably comprises less than 80% lower glycol, in which the feed stream of operative fluid to the membrane is provided at pressures between 10 and 2000 psig and temperatures between below ambient and about 120° C.

Non-aqueous, that is substantially undiluted, tri-ethylene glycol, di-ethylene glycol and ethylene glycol, tri-ethylene glycol being the most viscous of the three compounds, are much more viscous than, for example, antifreeze. Accordingly, a reverse osmosis system and process designed to treat used antifreeze is not capable of processing any of the contaminated ethylene glycol compounds in a substantially undiluted state.

SUMMARY OF THE INVENTION

It is an object of this invention to provide a process for purifying contaminated ethylene glycols, in particular tri-ethylene glycol, commonly found at gas production or gas storage sites.

It is another object of this invention to provide a process for purification of contaminated glycols contained in the drying tower/boiler reservoirs, that is in situ, as well as tri-ethylene glycols which have been removed and stored in contaminated tri-ethylene glycol holding tanks.

It is yet another object of this invention to provide a process for purifying ethylene glycols, in particular tri-ethylene glycol, which does not degrade the tri-ethylene glycol.

It is yet another object of this invention to provide a process for purifying contaminated ethylene glycols, in particular tri-ethylene glycol, utilizing reverse osmosis membranes.

These and other objects of this invention are achieved by a process for purification of substantially non-aqueous, contaminated glycol comprising heating the contaminated glycol to a temperature in the range of about 70° C. to about 100° C. and subjecting the contaminated glycol at said temperature range to a pressure between about 400 psig and about 650 psig, forming a pressurized contaminated glycol. The pressurized contaminated glycol is then passed through a reverse osmosis module comprising a reverse osmosis membrane, forming a permeate of substantially purified glycol and a retentate comprising contaminants separated from the contaminated glycol. In accordance with one embodiment of the process of this invention, the retentate is discharged from the reverse osmosis module, repressurized to about 400 psig to about 650 psig, and recirculated into the reverse osmosis module, forming an additional permeate of substantially purified glycol.

A critical feature of the process of this invention is the pressure range in which the process is carried out. The osmotic pressure of tri-ethylene glycol is about 2500 psi. Accordingly, contacting the reverse osmosis membrane in the reverse osmosis module with contaminated tri-ethylene glycol pressurized in the range of about 400 psig to about 650 psig constitutes a condition substantially outside of the range of pressures required for reverse osmosis to occur.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Although the process and apparatus discussed hereinbelow in connection with this invention are discussed in terms of their applicability to glycols, and in particular tri-ethylene glycol, it will be apparent to those skilled in the art that the process is also applicable to the purification of other substantially non-aqueous, high viscosity fluids. By non-aqueous or substantially non-aqueous, I mean a fluid having less than about 5% water. By high viscosity fluid, I mean a fluid having a viscosity greater than about 50 centipoises at ambient conditions. The viscosity of tri-ethylene glycol at 20° C. is about 50 centipoises.

The essential component of the system for conduct of the process of this invention is the reverse osmosis membrane, preferably assembled in either spiral-wound, tubular or hollow fine fiber module configurations. The membranes must be designed to accommodate temperatures above 70° C. and pressures up to about 650 psig.

In order to make the reverse osmosis membrane function in the process of this invention, a system must be employed which brings the contaminated tri-ethylene glycol to the membrane at the operating conditions required to pass the liquid through the membrane surface at an economically acceptable rate. The major components for such a treatment system as shown in FIG. 1 are a feed tank which allows heating of the feed stock to above about 70° C., a pre-filter to protect the process pump, a process pump capable of delivering the feed at or above about 70° C. and more than about 400 psig pressure, pressure vessels which are capable of withstanding the operating temperatures and pressures, and associated piping, valves, instrumentation and control systems to support and protect the equipment and process.

Treatment capacity is mainly a function of the amount of membrane area of the system. Additional production capability is provided by adding membrane surface to the system. This can be done by placing multiple membrane elements either in series or in parallel to accept the high pressure feed. The specific arrangement will be dictated by the hydraulic requirements of the reverse osmosis modules.

Figure 1:
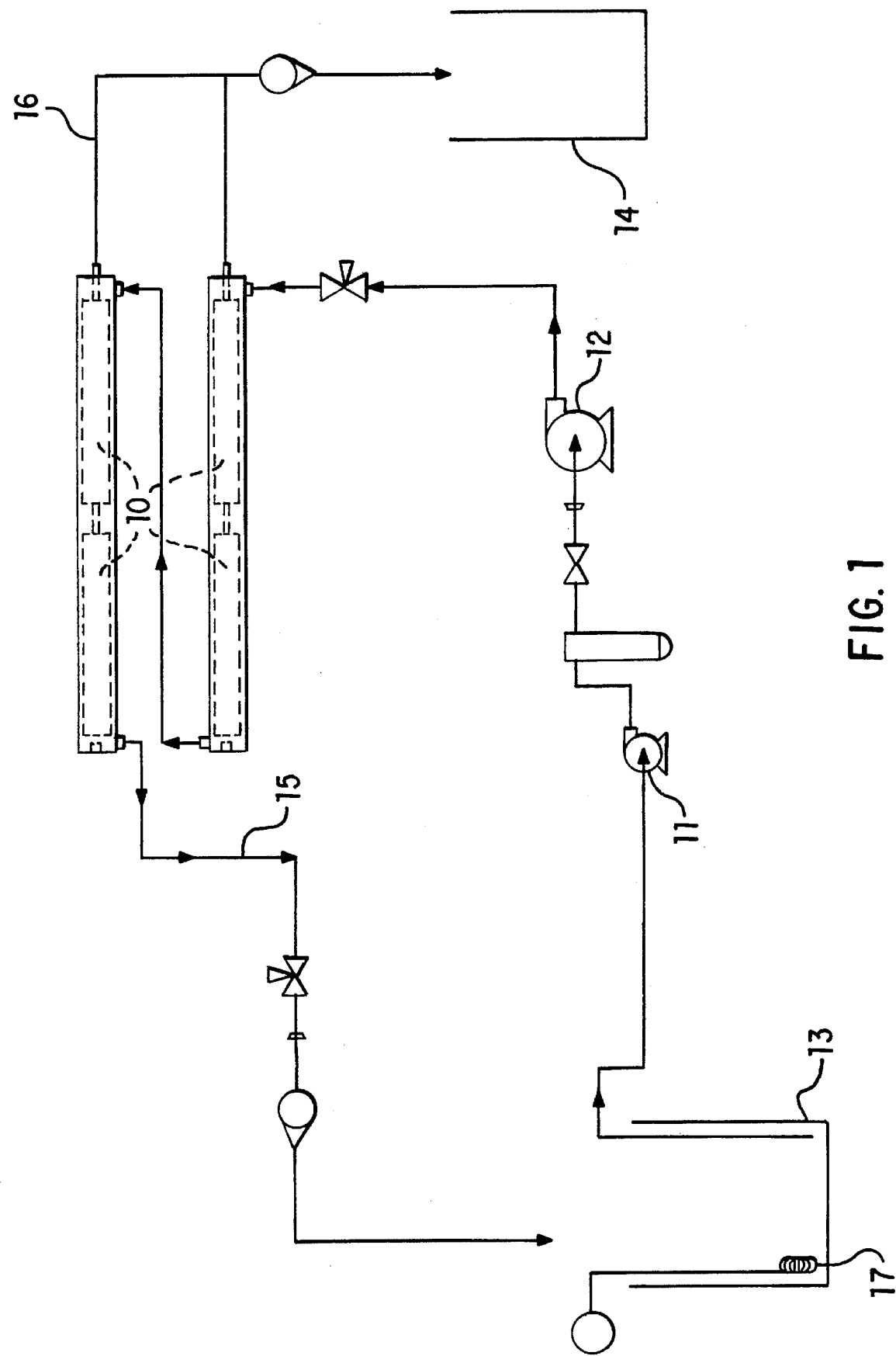
FIG. 1 is a schematic diagram of a reverse osmosis purification system suitable for application to the process of this invention.

FIG. 1 shows a schematic flow diagram of the process of this invention using four spiral-wound reverse osmosis membrane elements 10 in accordance with one embodiment of this invention. The processing of the contaminated glycol may be conducted on a batch or semi-batch basis. Contaminated glycols to be treated are heated by heater 17 in feed tank 13 to at least 70° C. and maintained at this temperature. The heated contaminated glycol is pumped from feed tank 13 by feed pump 11 to high pressure pump 12 by which the pressure of the heated contaminated glycol is raised to above about 400 psig. The pressurized heated contaminated glycol is then passed to reverse osmosis membrane elements 10, the flow rate and pressure at which the glycol is delivered to the reverse osmosis membranes being adjusted to meet the hydraulic demands of the reverse osmosis membranes and membrane elements employed. As the contaminated glycol passes along the surface of reverse osmosis membrane elements 10, at least a fraction of the glycol in the contaminated glycol stream penetrates to the interior of reverse osmosis membrane elements 10 and flows therefrom through permeate line 16 into product tank 14. Contaminants which do not pass through reverse osmosis membrane elements 10 remain in the contaminated glycol stream and are returned through retentate line 15 to feed tank 13 for further processing. This cycle is repeated until the desired amount of glycol has been permeated through reverse osmosis membrane elements 10. The amount of contaminated material which can be feasibly processed from each batch depends on the contamination level and pollutant characteristics in the contaminated glycol stream. The contaminated material is processed to a point where the concentration of the contaminants in the retentate becomes so high as to make further treatment counterproductive. This occurs when unacceptable amounts of contaminants pass through reverse osmosis membrane elements 10 with the permeate, resulting in repollution of the purified glycol permeate.

Figure 2:
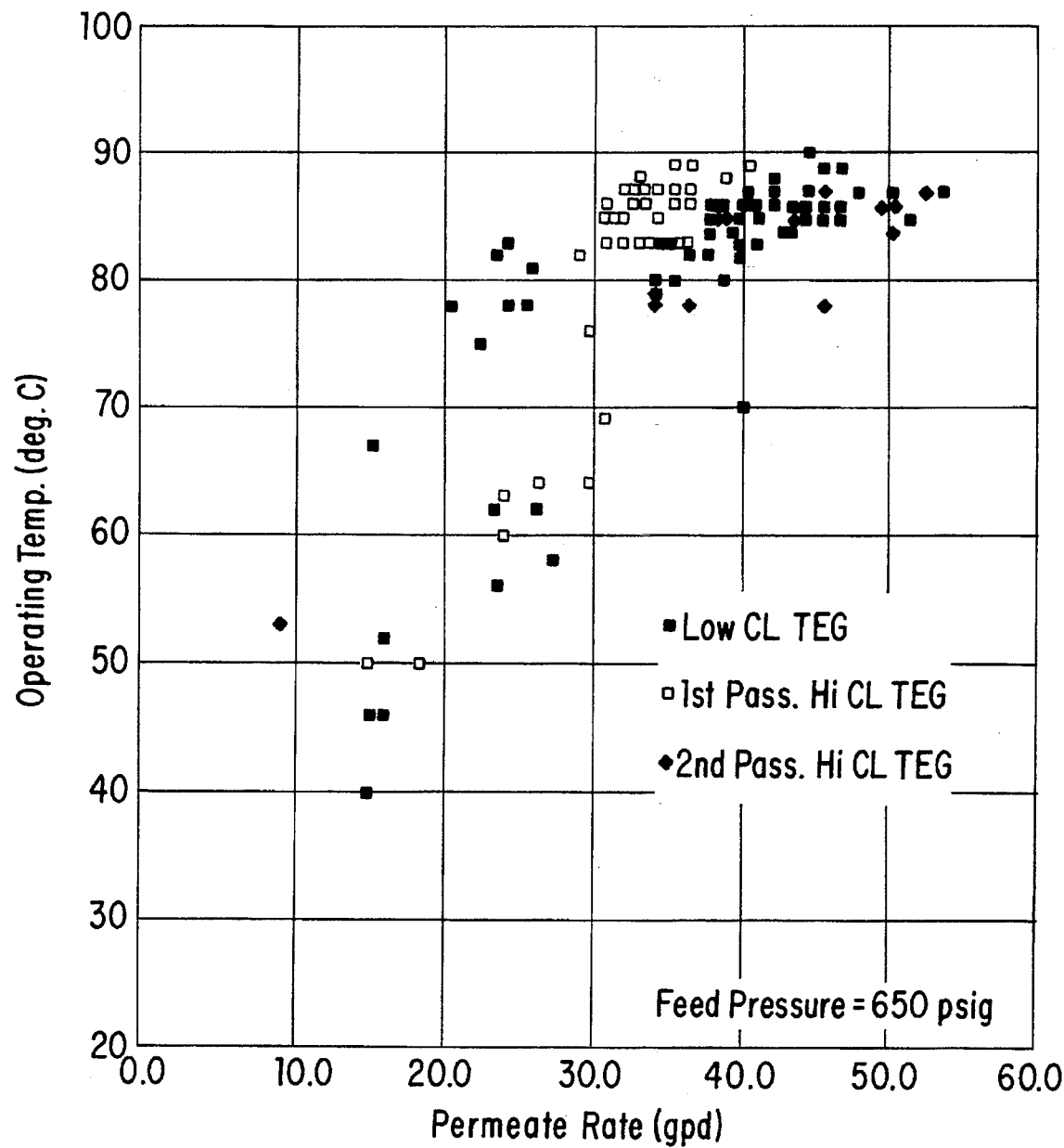
FIG. 2 is a graphic representation of the relationship between permeate and temperature.

In accordance with one embodiment of the process of this invention, the contaminated glycol is heated in feed tank 13 to a temperature in the range of about 70° C. to about 100° C. FIG. 2 shows that temperature has a significant influence on the performance of reverse osmosis membrane elements 10. When raising the operating temperature from about 40° C. to about 90° C., the flux rate increases three to four fold. Because the maximum operating temperature for the reverse osmosis membrane element employed was 90° C., operation above this temperature was not possible. FIG. 2 shows data points for three different feed types processed. As can be seen, no obvious trend or impact on performance can be identified for the different contaminated glycol feeds when they are processed at the same temperature and pressure condition.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for purification of a substantially non-aqueous, contaminated glycol comprising:

heating said substantially non-aqueous, contaminated glycol to a temperature in the range of about 70° C. to about 100° C.;

subjecting said substantially non-aqueous, contaminated glycol to a pressure between about 400 psig and about 650 psig, forming a pressurized substantially non-aqueous, contaminated glycol; and passing said pressurized substantially non-aqueous, contaminated glycol through a reverse osmosis module comprising a reverse osmosis membrane, forming a permeate of substantially purified glycol and a retentate comprising said contaminants separated from said substantially non-aqueous, contaminated glycol.

2. A process in accordance with claim 1, wherein said retentate is discharged from said reverse osmosis module, subjected to said pressure between about 400 psig and about 650 psig, and recirculated into said reverse osmosis module, forming an additional permeate of said substantially purified glycol.

3. A process in accordance with claim 1, wherein said substantially non-aqueous, contaminated glycol is selected from the group consisting of ethylene glycol, di-ethylene glycol, tri-ethylene glycol and mixtures thereof.

4. A process in accordance with claim 3, wherein said contaminated glycol is tri-ethylene glycol.

5. A process for purification of substantially non-aqueous, contaminated glycol comprising:

heating said substantially non-aqueous, contaminated glycol to a temperature in the range of about 70° C. to about 100° C., said substantially non-aqueous, contaminated glycol comprising at least one contaminant and at least one glycol; and passing said glycol through a reverse osmosis membrane at a pressure about 400 psig–650 psig, forming a permeate of purified glycol and a retentate comprising said at least one contaminant.

6. A process in accordance with claim 5, wherein said substantially non-aqueous: contaminated glycol is selected from the group consisting of ethylene glycol, di-ethylene glycol, tri-ethylene glycol and mixtures thereof.

7. A process in accordance with claim 6, wherein said substantially non-aqueous, contaminated glycol is tri-ethylene glycol.

8. A process for purification of a substantially non-aqueous, viscous, contaminated organic liquid comprising:

heating said substantially non-aqueous, viscous, contaminated organic liquid to a temperature in the range of about 70 C. to about 100 C.; and passing said heated substantially non-aqueous, viscous, contaminated organic liquid through a reverse osmosis membrane at a pressure in the range of about 400 psig to about 650 psig.

9. A process in accordance with claim 8, wherein said substantially non-aqueous, viscous contaminated organic liquid has a viscosity greater than about 50 centipoises at ambient temperatures.

10. A process in accordance with claim 8, wherein said substantially non-aqueous, viscous contaminated organic liquid is selected from the group consisting of ethylene glycol, di-ethylene glycol, tri-ethylene glycol and mixtures thereof.

11. A process in accordance with claim 10, wherein said substantially non-aqueous, viscous contaminated organic liquid is tri-ethylene glycol.

* * * * *